US012758522B2

(12) United States Patent
Chen et al.

(10) Patent No.: US 12,758,522 B2
(45) Date of Patent: Oct. 13, 2026

(54) INHIBITORS OF SGLT AND USES THEREOF

(71) Applicants: The Regents of the University of Michigan, Ann Arbor, MI (US); WAYNE STATE UNIVERSITY, Detroit, MI (US)

(72) Inventors: Yuqing Chen, Ann Arbor, MI (US); Jifeng Zhang, Ann Arbor, MI (US); Jie Xu, Ann Arbor, MI (US); Xiubin Liang, Ann Arbor, MI (US); Jian-Ping Jin, Detroit, MI (US); Fei Sun, Canton, MI (US)

(73) Assignees: The Regents of the University of Michigan, Ann Arbor, MI (US); WAYNE STATE UNIVERSITY, Detroit, MI (US)

(*) Notice: Subject to any disclaimer, the term of this patent is extended or adjusted under 35 U.S.C. 154(b) by 1051 days.

(21) Appl. No.: 17/639,831

(22) PCT Filed: Sep. 4, 2020

(86) PCT No.: PCT/US2020/049369

§ 371 (c)(1),
(2) Date: Mar. 2, 2022

(87) PCT Pub. No.: WO2021/046325

PCT Pub. Date: Mar. 11, 2021

(65) Prior Publication Data

US 2022/0323400 A1 Oct. 13, 2022

Related U.S. Application Data

(60) Provisional application No. 62/948,660, filed on Dec. 16, 2019, provisional application No. 62/895,800, filed on Sep. 4, 2019.

(51) Int. Cl.

| | |
|---|---|
| ***A61K 31/351*** | (2006.01) |
| ***A61P 3/10*** | (2006.01) |
| ***A61P 11/00*** | (2006.01) |

(52) U.S. Cl.
CPC .............. *A61K 31/351* (2013.01); *A61P 3/10* (2018.01); *A61P 11/00* (2018.01)

(58) Field of Classification Search
CPC .................................................... A61K 31/351
USPC .......................................................... 514/460
See application file for complete search history.

(56) References Cited

U.S. PATENT DOCUMENTS

| | | | |
|---|---|---|---|
| 3,989,816 | A | 11/1976 | Rajadhyaksha |
| 4,444,762 | A | 4/1984 | Rajadhyaksha |
| 2018/0104198 | A1 | 4/2018 | Rippmann et al. |
| 2018/0105498 | A1 | 4/2018 | Zemel et al. |
| 2018/0110762 | A1 | 4/2018 | Cox et al. |
| 2019/0192482 | A1 | 6/2019 | Minamino |

FOREIGN PATENT DOCUMENTS

| | | |
|---|---|---|
| CN | 103282030 | 9/2013 |
| WO | WO 2012/062698 | 5/2012 |
| WO | WO 2019/014645 | 1/2019 |
| WO | WO 2019/043613 | 3/2019 |

OTHER PUBLICATIONS

Zambrowicz et al., Clin Pharm and Therapeutics (2012), 92(2): 158-169.*
ADA Guidelines, Diabetes Care (2010), 33(12): 2697-2708.*
Liang X et al., The Beneficial Effects of Dual SGLT Inhibitors on Cystic Fibrosis Rabbits, Pediatric Pulmonology, vol. 54, No. Supplement 2, Oct. 1, 2019, 2 pages.
Cefalo, C. et al. "Sotagliflozin, the first dual SGLT inhibitor: current outlook and perspectives" Cardiovascular Diabetology, vol. 18, No. 20, pp. 1-14, Feb. 28, 2019.
Yavin, Y et al. "Effect of the SGLT2 Inhibitor Dapagliflozin on Potassium Levels in Patients with Type 2 Diabetes Mellitus: A Pooled Analysis" Diabetes Ther 7, 125-137 (2016).
Piperidou, A et al. "The effect of SGLT-2 inhibitors on albuminuria and proteinuria in diabetes mellitus: a systematic review and meta-analysis of randomized controlled trials" J Hypertension, abstract only. Jul. 2019;37(7):1334-1343.
International Search Report and Written Opinion for PCT/US2020/049369. Mailed Dec. 10, 2020. 10 pages.
Dalemans et al, Altered chloride ion channel kinetics associated with the delta F508 cystic fibrosis mutation. Nature. Dec. 19-26, 1991;354(6354):526-8.
Egan et al., Curcumin, a major constituent of turmeric, corrects cystic fibrosis defects. Science. Apr. 23, 2004;304(5670):600-2.
Ruan et al., Efficient Gene Editing at Major CFTR Mutation Loci. Mol Ther Nucleic Acids. Jun. 7, 2019;16:73-81.

* cited by examiner

*Primary Examiner* — Andrew D Kosar
(74) *Attorney, Agent, or Firm* — Casimir Jones, S.C.; Robert A. Goetz

(57) ABSTRACT

This invention is in the field of medicinal pharmacology. In particular, the present invention relates to pharmaceutical agents which function as inhibitors of sodium-glucose cotransporter (SGLT) activity. The invention further relates to methods of treating and/or ameliorating symptoms related to cystic fibrosis (CF), comprising administering to a subject (e.g., a human patient) a composition comprising one or more pharmaceutical agents which function as inhibitors of SGLT activity.

1 Claim, 12 Drawing Sheets

LX4211 treatment improves glucose tolerance in CF rabbits

FIG. 4

| Serum | WT (n=5) | CF (n=13-15) | CF+LX4211 (n=5) | normal range |
|---|---|---|---|---|
| Na+ (mmol/L) | 138.67±3.05 | 135.61±5.62 | 142.57±6.34 | 125-150 |
| **K+ (mmol/L)** | **4.36±0.25** | 3.14±0.30* | **4.67±0.21#** | 3.5-7 |
| Cl- (mmol/L) | 105.33±2.51 | 100.92±3.25 | 108.00±2.38 | 92-120 |
| Cr (mg/dL) | 0.87±0.10 | 0.61±0.24 | 1.15±0.21 | 0.5-2.6 |
| BUN (mg/dL) | 19.2±4.43 | 21.8±12.02 | 24.11±4.31 | 5.0-25 |
| **Gluc (mg/dL)** | **110.4±9.98** | 177.67±82.74* | **120.33±16.72#** | 74-148 |
| Trig (mg/dL) | 75.8±69.5 | 61.14±44.12 | 67.78±16.99 | 50-200 |
| **Chol (mg/dL)** | **31.6±9.76** | 114.8±56.6* | **56.45±22.24#** | 10-100 |
| AST (U/L) | 20.6±8.79 | 16.2±11.26 | 26.22±11.28 | 20-120 |
| ALT (U/L) | 61.8±9.04 | 35.27±10.86 | 61.11±19.33 | 25-65 |
| **ALP (U/L)** | 45.8±32.5 | 92.67±45.36* | 85.33±46.27 | 10.0-86 |
| **CPK (U/L)** | **573±63.85** | 1125.93±556.14* | **675.78±120.63#** | ---- |
| TBIL (mg/dL) | 0.05±0.01 | 0.05±0.02 | 0.05±0.01 | ---- |
| **ALB (g/dL)** | **3.76±0.59** | 2.65±0.53* | **3.64±1.20#** | 2.7-5 |
| Ca2+ (mg/dL) | 10.32±2.14 | 6.33±4.7 | 10.97±4.36 | 5.6-12.1 |
| **TPRO (g/dL)** | **6.02±0.57** | 4.19±1.39* | **6.37±0.34#** | 5-7.5 |

LX4211 (15 mg/kg/day) for 4 weeks, n=5

**p<0.05 CF VS WT; # p<0.05 LX4211 VS CF*

LX4211 treatment significantly attenuates hypokalemia and hyperglycemia of CF rabbits

WT n=5

CF n=13

CF+LX4211 (15 mg/kg/day) for 4 weeks, n=5

INHIBITORS OF SGLT AND USES THEREOF

This invention was made with government support under HL133162 awarded by the National Institutes of Health. The government has certain rights in the invention.

FIELD OF THE INVENTION

This invention is in the field of medicinal pharmacology. In particular, the present invention relates to pharmaceutical agents which function as inhibitors of sodium-glucose cotransporter (SGLT) activity. The invention further relates to methods of treating and/or ameliorating symptoms related to cystic fibrosis (CF), comprising administering to a subject (e.g., a human patient) a composition comprising one or more pharmaceutical agents which function as inhibitors of SGLT activity.

INTRODUCTION

An estimated 70,000 children and adults worldwide have Cystic Fibrosis (CF). CF is a life-threatening genetic disease caused by mutations in the gene encoding for the cystic fibrosis transmembrane conductance regulator (CFTR) protein. CFTR is a chloride channel that is expressed in multiple epithelial cell types. Mutations in the CFTR gene lead to an abnormal water and electrolytes transport through apical cell membranes of numerous exocrine tissues such as the lungs. Mutations of the CFTR gene have been classified in 5 classes of molecular defects of the protein: Class I, premature termination stop codon leading to complete absence of CFTR protein synthesis; Class II, arrested maturation and intracellular localization defect (processing block); Class III, defective activation and regulation of the chloride transport function (gating defect); Class IV, reduced conductance of the chloride channel; and Class V, reduced CFTR protein synthesis. The most common CFTR mutation is the deletion of the phenylalanine residue in position 508 of the polypeptide chain (mutation F508del, mutant protein F508del-CFTR), which belongs to Class II defect. This mutation is present on at least one allele in about 90% of CF patients, with almost 50% of the genotyped patients being F508del homozygous (see, Egan et al., Science, 2004, 304:600-602). The F508del mutation causes the failure of CFTR to traffic correctly to the plasma membrane because of protein misfolding that retains the protein in the endoplasmic reticulum. In addition, when the F508del-CFTR protein is correctly localized at the plasma membrane, it also has altered intrinsic chloride channel transport function relative to the wild type (WT) CFTR protein (see, Dalemans et al, Nature, 1991, 354:526-528).

In Oct. 2019, the Food and Drug Administration (FDA) approved Trikafta, a combination of CFTR potentiator VX-770 and CFTR correctors VX-445 and VX-661, which provides benefits to more than 90% of CF patients. While the entire community celebrated this milestone achievement 30 years after the discovery the CFTR gene, the consensus remains that this marks a new start other than the end ofefforts seeking deeper understanding of the disease and developing new and more effective therapeutics for all patients, as CF is still not cured.

Accordingly, improved methods and techniques are needed for treating and/or ameliorating CF.

The present invention addresses this need.

SUMMARY

Experiments conducted during the course of developing embodiments for the present invention utilized CF rabbits to examine the beneficial effects of SGLT inhibitor drugs on CF. It was demonstrated that SGLT inhibitor drugs such as LX4211 have beneficial effects on CF complications in multiple organ systems in an animal model of CF, thereby indicating that SGLT inhibitor drugs may provide therapeutic benefits to CF patients that have symptoms such as hypokalemia, hyperglycemia, dyslipidemia, hypoalbuminemia, and hypoproteinemia. Additional results demonstrated that LX4211 improves glucose tolerance in CF rabbits, LX4211 improves blood chemistry parameters in CF rabbits, that LX4211 benefits CF rabbits on electrolyte imbalance and lipid metabolism, that LX4211 does not affect weight gain and elongates CF rabbit lifespan. Indeed, such results demonstrate that that SGLT1 is upregulated in human CF airway lineage cells, and in many CF relevant tissues in CF rabbits; and that SGLT inhibitor LX4211 brought many beneficial effects on CF rabbits.

Accordingly, the present invention relates to pharmaceutical agents which function as inhibitors of SGLT activity, and methods of treating and/or ameliorating symptoms related to cystic fibrosis (CF) with such inhibitors of SGLT activity.

In certain embodiments, the present invention provides compositions comprising a pharmaceutical agent capable of inhibiting SGLT activity.

In certain embodiments, the present invention provides methods for inhibiting the activity of SGLT in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF.

In certain embodiments, the present invention provides methods for treating, ameliorating and/or preventing CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF.

In certain embodiments, the present invention provides methods for treating, ameliorating and/or preventing one or more symptoms related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the one or more symptoms related to CF includes, but is not limited to, hypokalemia, hyperglycemia, dyslipidemia, hypoalbuminemia, and hypoproteinemia.

In certain embodiments, the present invention provides methods for treating, ameliorating and/or preventing hypokalemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypokalemia related to CF.

In certain embodiments, the present invention provides methods for treating, ameliorating and/or preventing hyperglycemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hyperglycemia related to CF.

In certain embodiments, the present invention provides methods for treating, ameliorating and/or preventing dyslipidemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from dyslipidemia related to CF.

In certain embodiments, the present invention provides methods for treating, ameliorating and/or preventing hypoalbuminemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypoalbuminemia related to CF.

In certain embodiments, the present invention provides methods for treating, ameliorating and/or preventing hypoproteinemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypoproteinemia related to CF.

Such methods are not limited to treating a particular form or mutation related to CF. In some embodiments, the mutation is a any mutation related to a class 1A CTFR mutation (e.g., Dele2,3(21 kb) and 1717-1G→A). In some embodiments, the mutation is a any mutation related to a class 1B CTFR mutation (e.g., Gly542X and Trp1282X). In some embodiments, the mutation is a any mutation related to a class 2 CTFR mutation (e.g., Phe508del, Asn1303Lys, and Ala561Glu). In some embodiments, the mutation is a any mutation related to a class 3 CTFR mutation (e.g., Gly551Asp, Ser549Arg, and Gly1349Asp). In some embodiments, the mutation is a any mutation related to a class 4 CTFR mutation (e.g., Arg117His, Arg334Trp, and Ala455Glu). In some embodiments, the mutation is a any mutation related to a class 5 CTFR mutation (e.g., 3272-26A→G, 3849+10 kg C→T). In some embodiments, the mutation is a any mutation related to a class 6 CTFR mutation (e.g., c. 120del123 and rPhe580del).

In certain embodiments, the present invention provides kits comprising (1) a composition comprising a pharmaceutical agent capable of inhibiting SGLT activity, (2) a container, pack, or dispenser, and (3) instructions for administration.

Such compositions, methods, and kits are not limited to a particular type or kind of pharmaceutical agent capable of inhibiting SGLT activity. In some embodiments, the pharmaceutical agent capable of inhibiting SGLT activity is a small molecule, an antibody, nucleic acid molecule (e.g., siRNA, antisense oligonucleotide), or a mimetic peptide.

In some embodiments, the pharmaceutical agent capable of inhibiting SGLT activity is selected from, for example, Phlorizin, Canagliflozin ((2S,3R,4R,5S,6R)-2-{3-[5-[4-Fluoro-phenyl)-thiophen-2-ylmethyl]-4-methyl-phenyl}-6-hydroxymethyl- tetrahydro-pyran-3,4,5-triol), Dapagliflozin ((2S,3R,4R,5S,6R)-2-[4-chloro-3-(4-ethoxybenzyl)phenyl]-6-(hydroxymethyl)-tetrahydro-2H-pyran-3,4,5- triol), Empagliflozin ((2S,3R,4R,5S,6R)-2-[4-chloro-3-[[4-[(3S)-oxolan-3-yl]oxyphenyl]methyl]ph-enyl]-6- (hydroxymethyl)oxane-3,4,5-triol), Remogliflozin (5-methyl-4-[4-(1-methylethoxy)benzyl]-1-(1-methylethyl)-1H-pyrazol-3-yl 6-O-(ethoxycarbonyl)-β-D-glucopyranoside),Sergliflozin (2-(4-methoxybenzyl)phenyl 6-O-(ethoxycarbonyl)-β-D-glucopyranoside), and Tofogliflozin ((1S,3'R,4'S,5'S,6'R)-6-(4-Ethylbenzyl)-6'-(hydroxymethyl)-3',4',5',6'-te-trahydro-3H-spiro[2- benzofuran-1,2'-pyran]-3',4',5'-triol hydrate (1:1)), and Sotagliflozin (LX4211), or a pharmaceutically acceptable salt thereof.

BRIEF DESCRIPTION OF THE DRAWINGS

FIG. 4 demonstrated the beneficial effects of LX4211 on electrolyte imbalance and disorders of glucose and lipid metabolism in CF rabbit model.

DETAILED DESCRIPTION OF THE INVENTION

Figure 1:
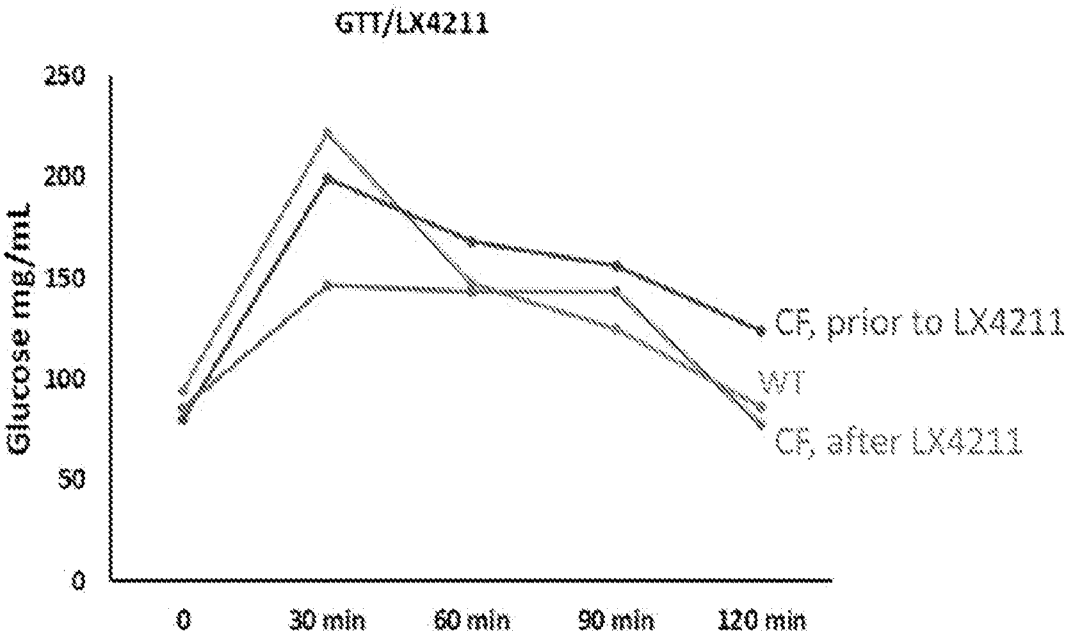
FIG. 1 shows that LX4211 restored glucose tolerance of CF rabbits.

Cystic Fibrosis (CF) is a lethal autosomal recessive disease caused by mutations in the gene encoding the cystic fibrosis transmembrane conductance regulator (CFTR). CF patients suffer primarily from CF lung diseases, as well as CF related liver diseases, CF related diabetes, CF related gastric intestinal diseases and others. Electrolyte abnormalities and acid-base disturbance are also associated with CF including hypokalemia and metabolic alkalosis. Sodium-glucose cotransporter (SGLT) inhibitors, including selective SGLT2 inhibitors and dual SGLT1/2 inhibitors, have becoming mainstream therapy for diabetes. The effects of SGLT inhibitors in CF have not been systematically tested.

Experiments conducted during the course of developing embodiments for the present invention utilized CF rabbits to examine the beneficial effects of SGLT inhibitor drugs on CF. It was demonstrated that SGLT inhibitor drugs such as LX4211 have beneficial effects on CF complications in multiple organ systems in an animal model of CF, thereby indicating that SGLT inhibitor drugs may provide therapeutic benefits to CF patients that have symptoms such as hypokalemia, hyperglycemia, dyslipidemia, hypoalbuminemia, and hypoproteinemia. Additional results demonstrated that LX4211 improves glucose tolerance in CF rabbits, LX4211 improves blood chemistry parameters in CF rabbits, that LX4211 benefits CF rabbits on electrolyte imbalance and lipid metabolism, that LX4211 does not affect weight gain and elongates CF rabbit lifespan. Indeed, such results demonstrate that that SGLT1 is upregulated in human CF airway lineage cells, and in many CF relevant tissues in CF rabbits; and that SGLT inhibitor LX4211 brought many beneficial effects on CF rabbits.

Accordingly, the present invention relates to pharmaceutical agents which function as inhibitors of SGLT activity, and methods of treating and/or ameliorating symptoms related to cystic fibrosis (CF) with such inhibitors of SGLT activity.

In certain embodiments, the present invention provides methods for inhibiting the activity of SGLT in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF.

In certain embodiments, the present invention provides methods for treating, ameliorating and/or preventing CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF.

In certain embodiments, the present invention provides methods for treating, ameliorating and/or preventing one or more symptoms related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the one or more symptoms related to CF includes, but is not limited to, hypokalemia, hyperglycemia, dyslipidemia, hypoalbuminemia, and hypoproteinemia.

In certain embodiments, the present invention provides methods for treating, ameliorating and/or preventing hypokalemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypokalemia related to CF.

In certain embodiments, the present invention provides methods for treating, ameliorating and/or preventing hyperglycemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hyperglycemia related to CF.

In certain embodiments, the present invention provides methods for treating, ameliorating and/or preventing dyslipidemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from dyslipidemia related to CF.

In certain embodiments, the present invention provides methods for treating, ameliorating and/or preventing hypoalbuminemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypoalbuminemia related to CF.

In certain embodiments, the present invention provides methods for treating, ameliorating and/or preventing hypoproteinemia related to CF in a subject, comprising administering to the subject a composition comprising a pharmaceutical agent capable of inhibiting SGLT activity. In some embodiments, the subject is a human subject. In some embodiments, the subject is a human subject suffering from or at risk of suffering from any form and/or mutation related to CF. In some embodiments, the subject is a human subject suffering from or at risk of suffering from hypoproteinemia related to CF.

Such methods are not limited to treating a particular form or mutation related to CF. In some embodiments, the mutation is a any mutation related to a class 1A CTFR mutation (e.g., Dele2,3(21 kb) and 1717-1G→A). In some embodiments, the mutation is a any mutation related to a class 1B CTFR mutation (e.g., Gly542X and Trp1282X). In some embodiments, the mutation is a any mutation related to a class 2 CTFR mutation (e.g., Phe508del, Asn1303Lys, and Ala561Glu). In some embodiments, the mutation is a any mutation related to a class 3 CTFR mutation (e.g., Gly551Asp, Ser549Arg, and Gly1349Asp). In some embodiments, the mutation is a any mutation related to a class 4 CTFR mutation (e.g., Arg117His, Arg334Trp, and Ala455Glu). In some embodiments, the mutation is a any mutation related to a class 5 CTFR mutation (e.g., 3272-26A→G, 3849+10 kg C→T). In some embodiments, the mutation is a any mutation related to a class 6 CTFR mutation (e.g., c. 120del123 and rPhe580del).

The present invention is not limited to particular types or kinds of pharmaceutical agents which function as inhibitors of SGLT activity. In some embodiments, the pharmaceutical agent capable of inhibiting SGLT activity is a small molecule, an antibody, nucleic acid molecule (e.g., siRNA, antisense oligonucleotide), or a mimetic peptide.

In some embodiments, the pharmaceutical agent capable of inhibiting SGLT activity is selected from, for example, Phlorizin, Canagliflozin ((2S,3R,4R,5S,6R)-2-{3-[5-[4-Fluoro-phenyl)-thiophen-2-ylmethyl]-4-methyl-phenyl}-6-hydroxymethyl-tetrahydro- pyran-3,4,5-triol), Dapagliflozin ((2S,3R,4R,5S,6R)-2-[4-chloro-3-(4-ethoxybenzyl)phenyl]-6-(hydroxymethyl)-tetrahydro-2H-pyran-3,4,5-triol), Empagliflozin ((2S,3R,4R,5S,6R)-2-[4-chloro-3-[[4-[(3S)-oxolan-3-yl]oxyphenyl]methyl]ph-enyl]-6- (hydroxymethy) oxane-3,4,5-triol), Remogliflozin (5-methyl-4-[4-(1-methylethoxy)benzyl]-1-(1-methylethyl)-1H-pyrazol-3-yl 6-O-(ethoxycarbonyl)-β-D-glucopyranoside), Sergliflozin (2-(4-methoxybenzyl)phenyl 6-O-(ethoxycarbonyl)-β-D-glucopyranoside), and Tofogliflozin ((1S,3'R,4'S,5'S,6'R)-6-(4-Ethylbenzyl)-6'-(hydroxymethyl)-3',4',5',6'-te-trahydro-3H- spiro[2benzofuran-1,2'-pyran]-3', 4', 5'-triol hydrate (1:1)), and Sotagliflozin (LX4211), or a pharmaceutically acceptable salt thereof.

An important aspect of the present invention is that the compositions of the present invention (e.g., compositions comprising pharmaceutical agents which function as inhibitors of SGLT activity) are useful in treating CF and symtoms related to CF (e.g., hypokalemia, hyperglycemia, dyslipidemia, hypoalbuminemia, and hypoproteinemia).

Some embodiments of the present invention provide methods for administering an effective amount of a composition comprising a pharmaceutical agent which functions as an inhibitor of SGLT activity of the invention and at least one additional therapeutic agent (including, but not limited to, any pharmaceutical agent useful in treating CF and/or symtoms related to CF (e.g., hypokalemia, hyperglycemia, dyslipidemia, hypoalbuminemia, and hypoproteinemia).

Compositions within the scope of this invention include all compositions wherein the pharmaceutical agents which function as inhibitors of SGLT activity are contained in an amount that is effective to achieve its intended purpose. While individual needs vary, determination of optimal ranges of effective amounts of each component is within the skill of the art. Typically, the pharmaceutical agents which function as inhibitors of SGLT activity (e.g., small molecules, antibodies, mimetic peptides) may be administered to mammals, e.g. humans, orally at a dose of 0.0025 to 50 mg/kg, or an equivalent amount of the pharmaceutically acceptable salt thereof, per day of the body weight of the mammal being treated for disorders responsive to inhibition of SGLT activity. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 3000 mg, for example, about 0.1 to about 100 mg of the SGLT activity inhibiting agent. The unit dose may be administered one or more times daily as one or more tablets or capsules each containing from about 0.1 to about 10 mg, conveniently about 0.25 to 50 mg of the SGLT activity inhibiting agent (e.g., mimetic peptide, small molecule) or its solvates.

In a formulation (e.g., intravenous formulation, intraperitoneal formulation, intramuscular formulation, subcutaneous formulation, injection formulation, topical formulation, oral formulation, etc.), the SGLT activity inhibiting agent (e.g., mimetic peptide, small molecule) may be present at a concentration of about 0.01 to 100 mg per gram of carrier. In a one embodiment, the SGLT activity inhibiting agent (e.g., mimetic peptide, small molecule) is present at a concentration of about 0.07-1.0 mg/ml, for example, about 0.1-0.5 mg/ml, and in one embodiment, about 0.4 mg/ml.

In addition to administering the SGLT activity inhibiting agent (e.g., mimetic peptide, small molecule) as a raw chemical, SGLT activity inhibiting agents (e.g., mimetic peptides, small molecule) of the invention may be administered as part of a pharmaceutical preparation containing suitable pharmaceutically acceptable carriers comprising excipients and auxiliaries which facilitate processing of the SGLT activity inhibiting agents into preparations which can be used pharmaceutically. The preparations, particularly those preparations which can be administered in any desired manner (e.g., intravenous, intraperitoneal, intramuscular, subcutaneous, topical, oral, etc.) and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient that may experience the beneficial effects of a SGLT activity inhibiting agent (e.g., mimetic peptides, small molecules) of the invention. Foremost among such patients are mammals, e.g., humans, although the invention is not intended to be so limited. Other patients include veterinary animals (cows, sheep, pigs, horses, dogs, cats and the like).

The SGLT activity inhibiting agents (e.g., mimetic peptides, small molecules) and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye-stuffs or pigments may be added to the tablets or dragee coatings, for example, for identification or in order to characterize combinations of active mimetic peptide doses.

Other pharmaceutical preparations that can be used orally include push-fit capsules made of gelatin, as well as soft, sealed capsules made of gelatin and a plasticizer such as glycerol or sorbitol. The push-fit capsules can contain the active mimetic peptides in the form of granules that may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules that consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof All patents, patent applications and publications cited herein are fully incorporated by reference herein in their entirety.

EXPERIMENTAL

Example I

This example demonstrates the beneficial effects of SGLT inhibitor LX4211 in treating CF.

To determine whether the dual SGLT1/2 inhibitor LX4211 (

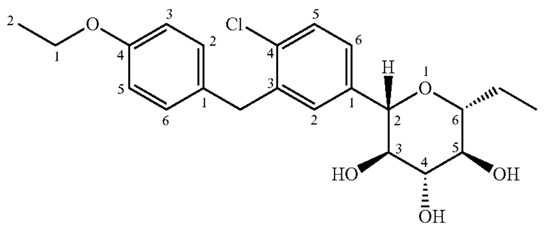

(2S,3R,4R,5S,6R)-2-(4-chloro-3-(4-ethoxybenzyl)phenyl)-6-(methylthio)tetrahydro-2H-pyran-3,4,5-triol )

) has beneficial effects on treating CF, 5 CF rabbits were daily gavaged with LX4211 (15 mg/kg/day) for 4 weeks. The intravenous glucose tolerance test (IVGTT) and insulin tolerance test (ITT) were performed before treatment and at 4 weeks after treatment. Urine was collected daily to assess urinary glucose excretion. Blood was collected biweekly for the analysis of chemical panels including glucose, insulin, liver function, kidney function, lipid profiles and electrolytes. At the end of the experiment, the organ tissues of CF rabbits were collected for histology staining.

All five CF rabbits showed no obvious adverse response to the LX4211 treatment. As expected, urine glucose levels spiked starting D1 after the treatment. Daily abdominal palpation of all animals revealed softening of the abdominal. Because most CF rabbits eventually die of gut obstruction for which abdominal hardening (which can be felt by palpation) has been used as a clinical sign, such softening may indicate beneficial effects on alleviating GI obstruction, although further studies are needed to confirm this predication.

Figure 2:
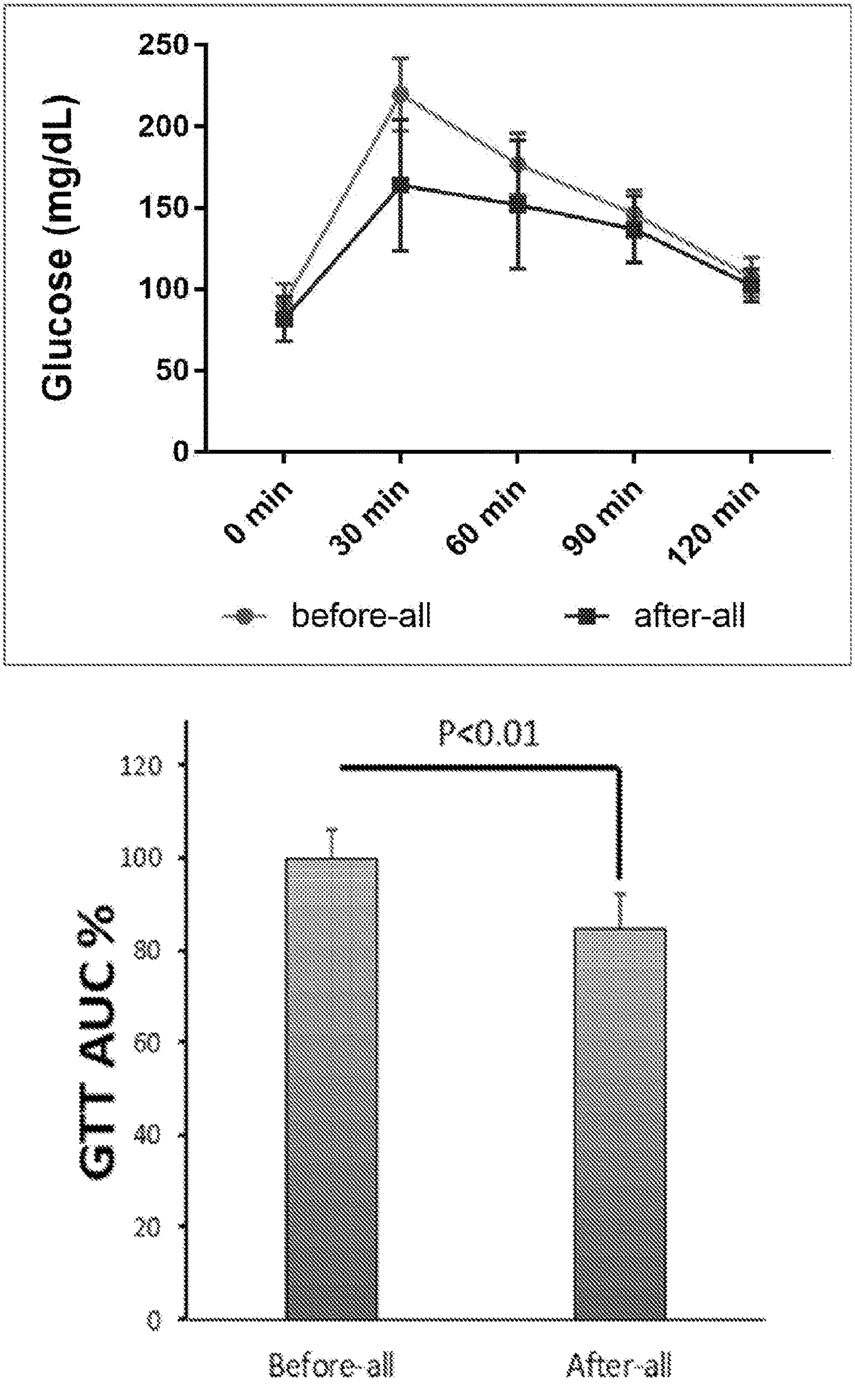
FIG. 2 demonstrates that LX4211 treatment improved glucose tolerance in CF rabbits.
Figure 3:
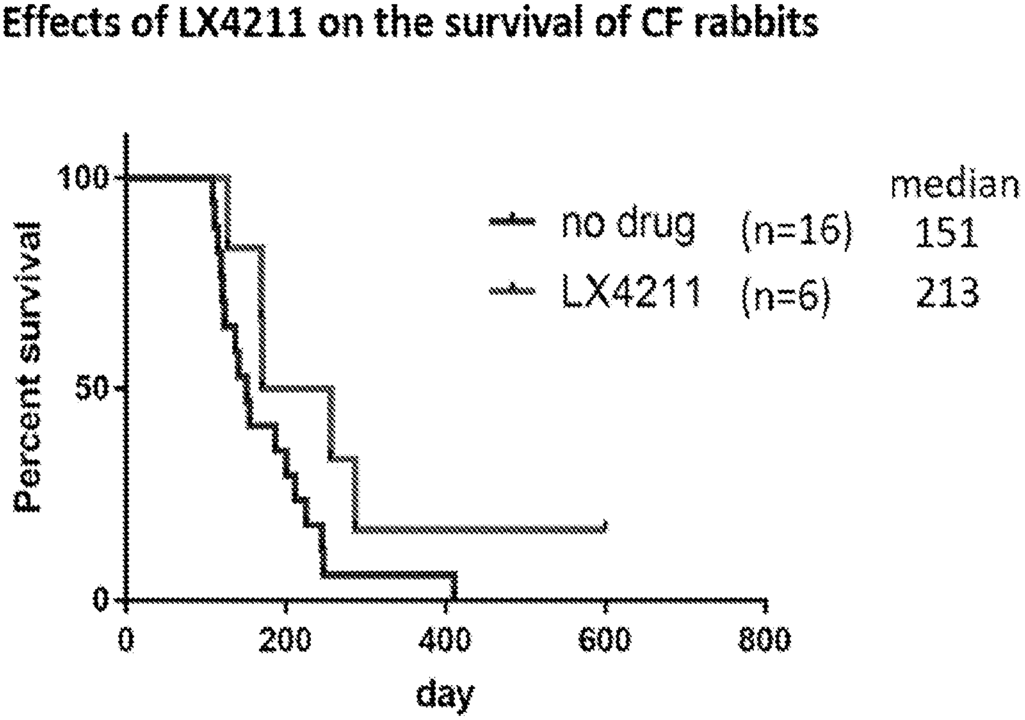
FIG. 3 demonstrates that LX4211 treatment resulted in improved survival length in CF rabbits.

FIG. 1 shows that LX4211 restored glucose tolerance of CF rabbits. One CF rabbit showed definite signs of CF related diabetes (CFRD) prior to the LX4211 treatment (red line) wherein the GTT response was restored to normal after the treatment (green line). This result indicated that SGLT inhibitors bring clinical benefits to CFRD. FIG. 2 additional demonstrates that LX4211 treatment improved glucose tolerance in CF rabbits. FIG. 3 demonstrates that LX4211 treatment resulted in improved survival length in CF rabbits.

Figure 5:
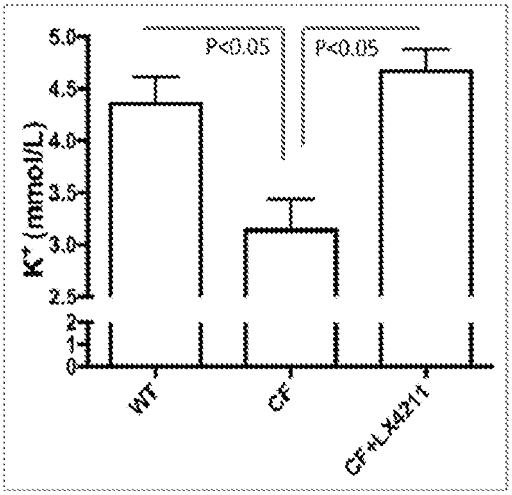
FIG. 5 shows that LX4211 treatment significantly attenuated hypokalemia and hyperglycemia of CF rabbits.
Figure 5:
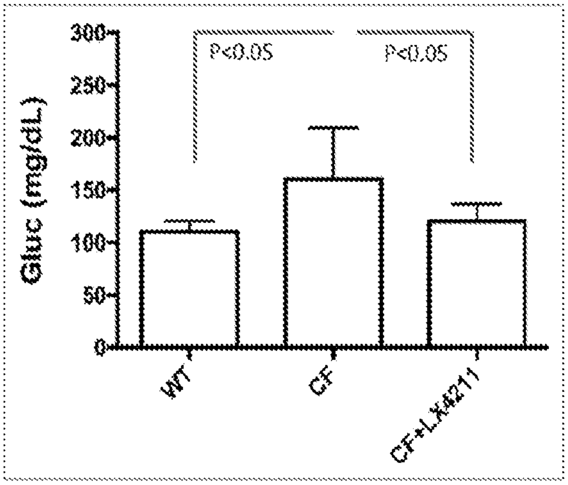
Figure 6:
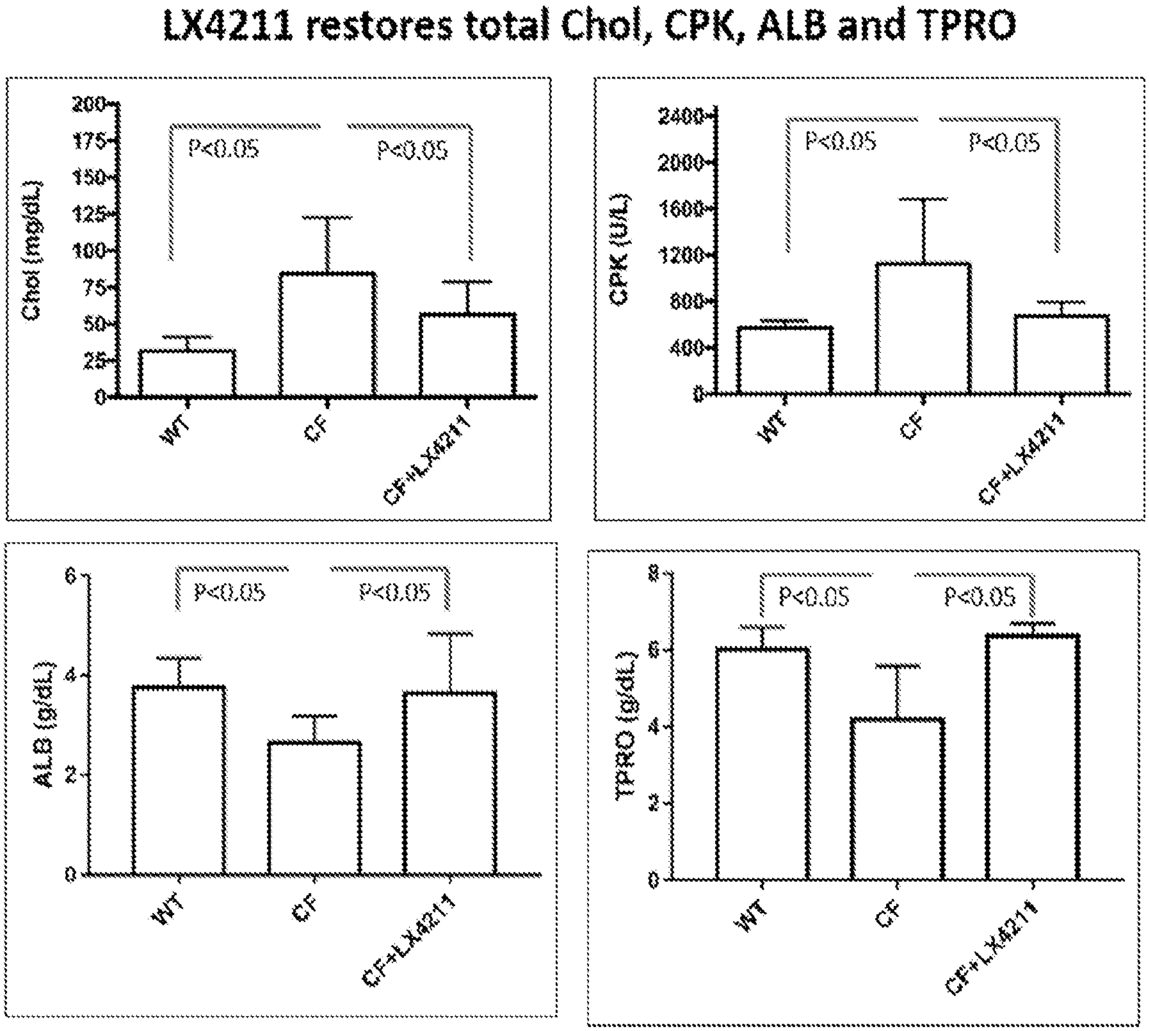
FIG. 6 shows that LX4211 restored total Chol (Cholesterol), CPK (Creatine Kinase), ALB (Albumin) and TPRO (Total Protein).

LX4211 was shown to provide beneficial effects on electrolyte imbalance and disorders of glucose and lipid metabolism in CF rabbits. As shown in FIG. 4, CF rabbits, compared with WT, presented many abnormalities in metabolic parameters including lower serum potassium, higher triglyceride, cholesterol and glucose. Abnormalities of serum ALP, CPK and Calcium were also detected in CF rabbits. LX4211 treatment significantly attenuated hypokalemia and hyperglycemia of CF rabbits. Moreover, the significant rescue effects on triglyceride, cholesterol, CPK and Calcium were observed in CF animals after the start of LX4211. These results demonstrated the beneficial effects of SGLT2 dual inhibitor, LX4211, on electrolyte imbalance and disorders of glucose and lipid metabolism in CF rabbit model. FIG. 5 shows that LX4211 treatment significantly attenuated hypokalemia and hyperglycemia of CF rabbits. FIG. 6 shows that LX4211 restored total Chol, CPK, ALB and TPRO.

Example II

This example demonstrates that SGLT1 is upregulated in CF relevant tissues in CF rabbits.

SGLT1 and SGLT2 transcription (i.e. mRNA) levels in CF and WT rabbits was first determined. The SGLT2 expression, similar to that reported in humans and other animals, is largely restricted to the kidney, and there is no difference in between CF and WT rabbits. Interesting SGLT1 mRNA levels are elevated in several CF relevant tissues including trachea, intestine and liver (FIG. 7A-D). Western blot showed that the protein levels of SGLT1 are also higher in the intestine, pancreas (FIG. 7E) and lung (FIG. 7F) tissues in CF rabbits than in WT ones. Consistently immunohistostaining confirmed the upregulation of SGLT1 in the intestine and pancreas of CF rabbits than of WT ones. Together, these data show that SGLT1 is upregulated in CF relevant tissues in CF rabbits.

Example III

This example demonstrates SGLT1 is upregulated in CF patient derived cells.

Experiments were conducted that examined if SGLT1 expression is also regulated in human patient derived airway lineage cells. Experiments were conducted that examined SGLT1 protein levels in CF bronchial epithelial (CFBE) cells as well as CF lung organoids derived from CF patient specific iPSCs as previously reported (see, J. Ruan et al., Mol Ther Nucleic Acids https://doi.org/10.1016/j.omtn.2019.02.006 (2019)).

Figure 8:
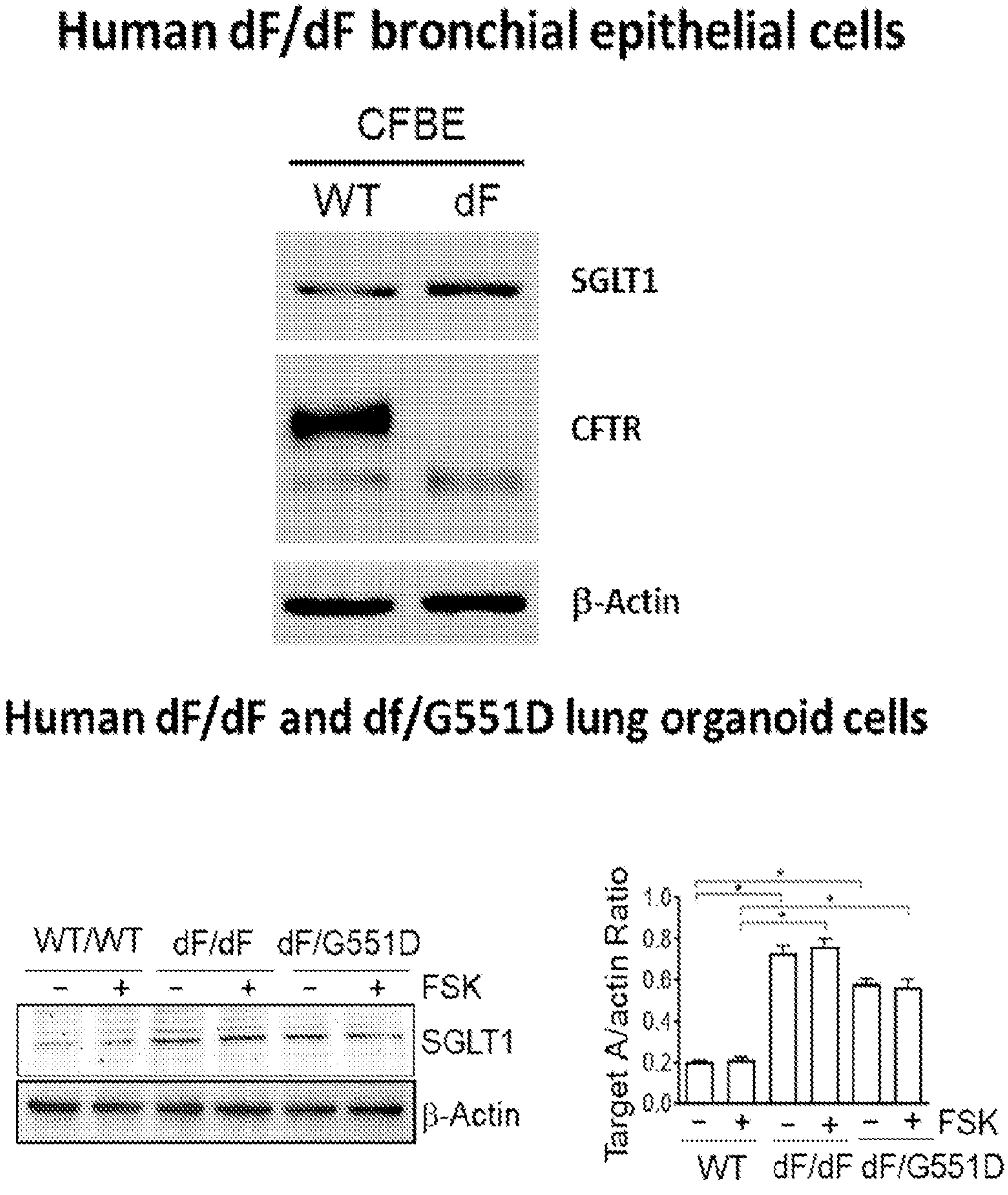
FIG. 8. SGLT1 protein levels in CF patient derived airway lineage cells. Left panel: SGLT1 and CFTR levels in CFBE cells. Right panel: SGLT1 protein levels in lung organoids of different genotypes (WT/WT, dF/dF and dF/G551D) with or without Forskolin (FSK) stimulation.

The CFTR bandings in the CFBE cells were consistent with their genotypes. The SGLT1 signals were reversely correlated with those of CFTR: high in the CFBE-dF cells but low CFBE-WT cells (FIG. 8, left panel). Consistently, in both dF/dF and dF/G551D lung orgaonids, the SGLT1 levels were significantly higher than those in the WT/WT organoids (FIG. 8, right panel).

These data show that as observed in CF rabbits, SGLT1 is upregulated in CF patient derived airway lineage cells. Together, these data suggest that SGLT1 is indicative of a therapeutic target in CF.

Example IV

This example demonstrates that Sotagliflozin (Sota) (LX4211) improves glucose tolerance in CF rabbits.

The finding that SGLT1 is elevated in several CF relevant tissues strongly suggested a testing of SGLT1 inhibitor drug on CF rabbits.

An initial hypothesis was that SGLT1 inhibition may attenuate the CFRD conditions. However, due to the lack of a SGLT1 inhibitor then, a dual inhibitor Sota was used which inhibits SGLT2 and SGLT1.

Figure 9:
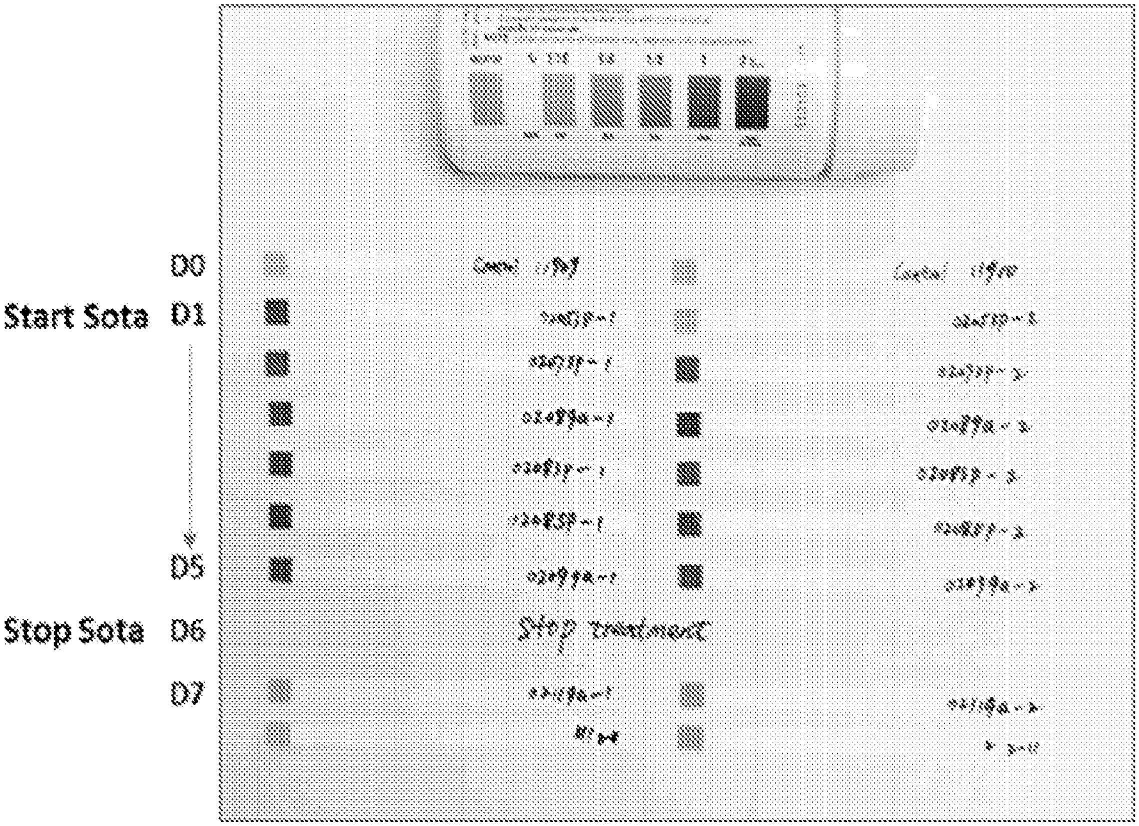
FIG. 9. Urine sugar levels in WT rabbits after Sota treatment.

Experiments were conducted that first examined the physiological responses of rabbits to Sota by measuring the urine sugar levels to assess urinary glucose excretion (FIG. 9). Sota was given to WT rabbits (n=2) daily for five days. A spike of urine sugar level was seen the second day (D1) and remained high during the treatment days (D1-D5). Upon retrieval of the drug, the urine sugar level immediately returned to normal (D7). This confirmed that rabbits respond to Sota similarly as rodents and human patients.

Figure 10:
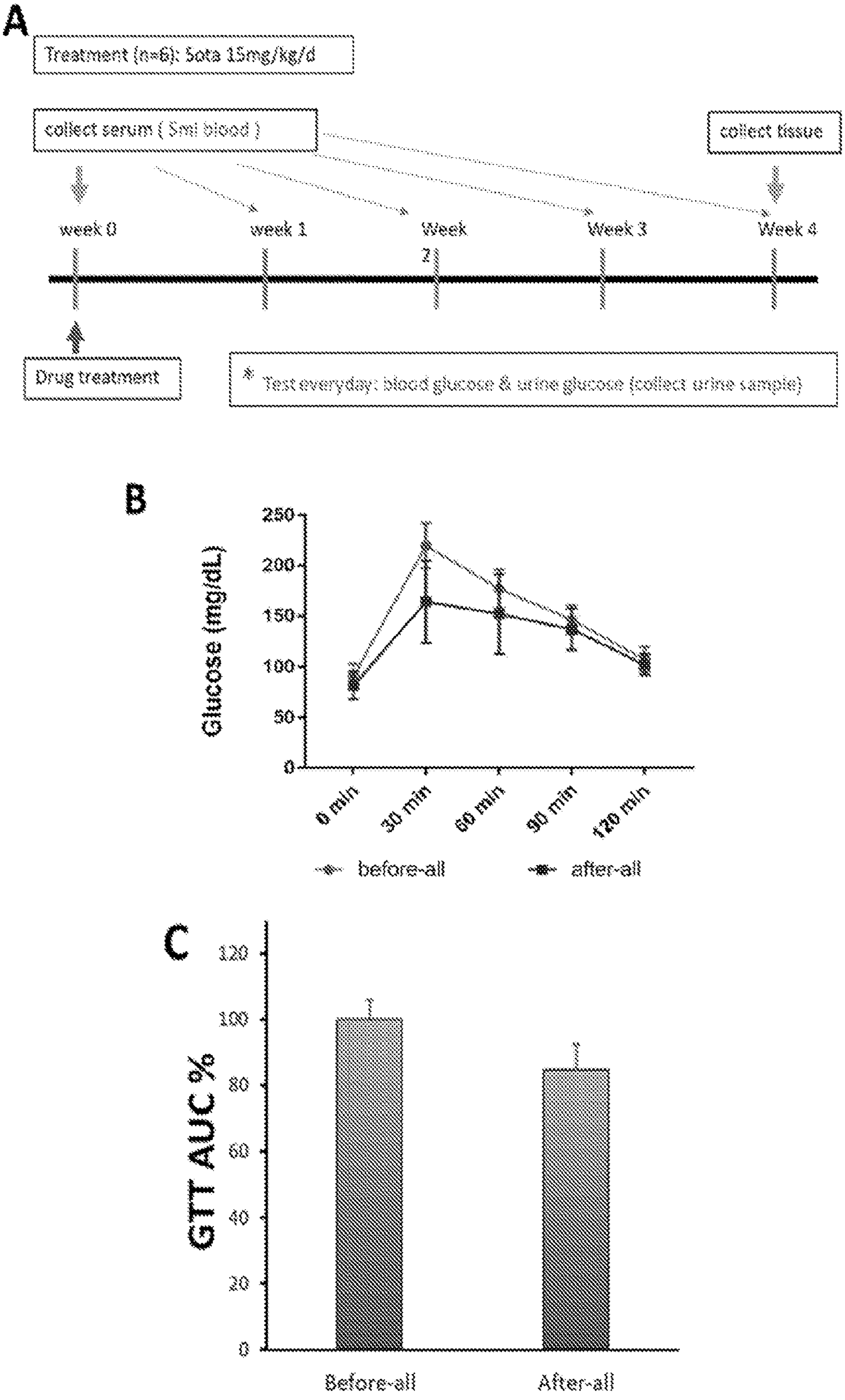
FIG. 10A-C. Sota treatment regime and its effects GTT tests. (A) Sota treatment regime. (B) GTT curve of CF rabbits prior to (red line) and after Sota-treatment (blue line). (C) Summary of area under curve (AUC).

Experiments were conducted that next proceeded to treat CF rabbits (n=6) with Sota (15 mg/kg/day) by daily gavage for 4 weeks (FIG. 10A). The IVGTT test was performed prior to and 4 weeks after treatment. Sota-treated animals showed a significantly higher blood glucose elimination rate than those in the non-treatment group (FIGS. 10B & C), demonstrating Sota's beneficial effects on glucose metabolism in CF rabbits.

Example V

This example demonstrates that Sota improves blood chemistry parameters in CF rabbits.

It is known that many CF patients show abnormalities in their blood chemistry tests. Blood chemistry in CF rabbits was also examind. In one study, blood was collected from 5 CF rabbits for the analysis of chemical panels including electrolytes, glucose and other metabolic parameters, and compared with those of WT rabbits (n=15). CF rabbits presented many abnormalities in metabolic parameters including lower serum potassium (WT 4.35±0.25 vs. CF 3.14±0.3, $p<0.05$), higher triglyceride (WT 75.8±69.5 vs. CF 447.0±76.6, $p<0.05$), cholesterol (WT 31.6±9.76 vs. CF 177.2±206.3, $p<0.05$) and glucose (WT 110.4±9.99 vs. CF 160.6±37.5, $p<0.05$). Abnormalities of serum ALP, CPK and Calcium were also detected in CF rabbits.

To evaluate if Sota has any effects on the blood chemistry parameters of CF rabbits, experiments were conducted wherein 5 CF rabbits were treated with Sota for 10 weeks. CF rabbits in the control group (n=5) did not receive any Sota treatment.

Figure 7:
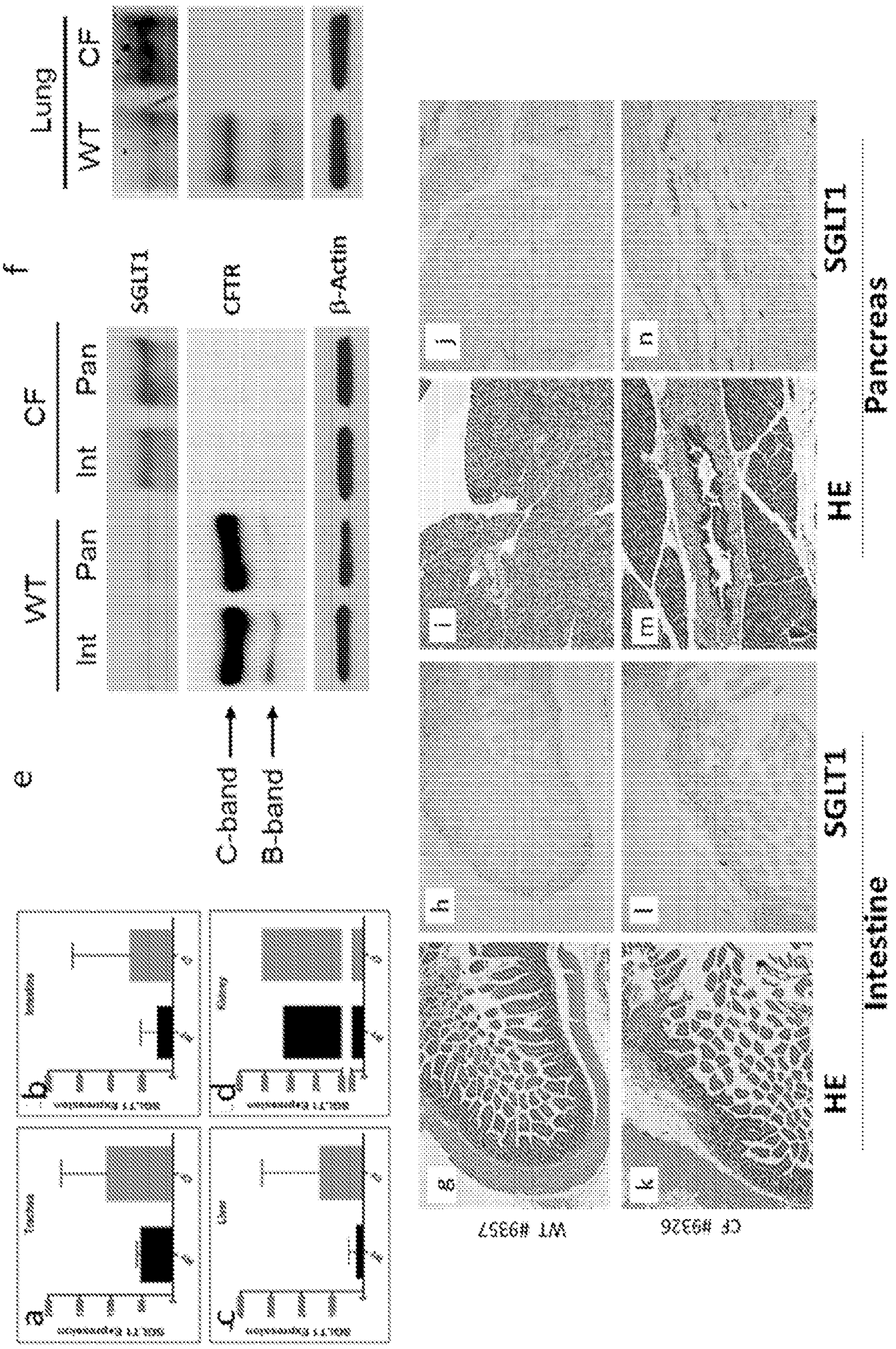
FIG. 7A-N shows SGLT1 expressions in CF rabbit tissues. (a-d) mRNA levels in different tissues of CF and WT rabbits. (e) SGLT1 and CFTR protein levels in the intestine (int) and pancreases (pan) tissues of CF and WT rabbits. (f) SGLT and CFTR protein levels in the lungs of WT and CF rabbits. (g-n) immunostaining of SGLT1 (brown color) in the intestine and pancreas of WT and CF rabbits.
Figure 11:
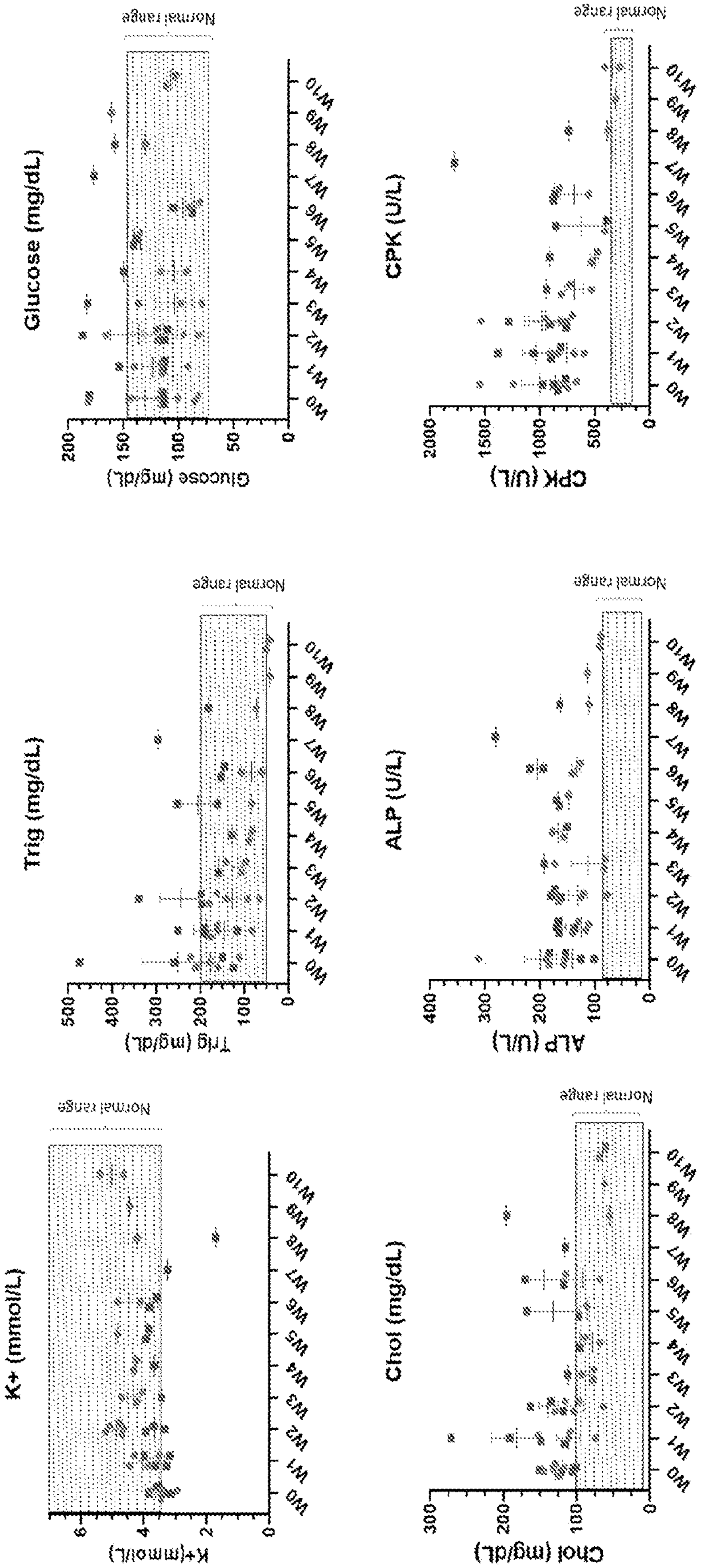
FIG. 11. Selected blood chemistry results of CF rabbits treated (green dots) or not treated (red dots) with Sota. Grey box: normal range.

The Sota treatment significantly improved the imbalanced/abnormal parameters such as K+, Trig, Glucose, Chol, ALP and CPK (FIG. 11). In the control group animals, these parameters gradually worsened; whereas in the Sota-treated group, these parameters returned to the normal ranges in general (FIG. 7). These unexpected findings indicate that Sota treatment benefit CF rabbits beyond the glucose metabolism, and in particular, on electrolyte imbalance and lipid metabolism.

Example VI

This example demonstrates Sota does not affect weight gain and elongates CF rabbit lifespan.

One striking finding from the experiment is that Sota did not affect the weight gain, and that Sota significantly elongated the lifespan of CF rabbits.

Figure 12:
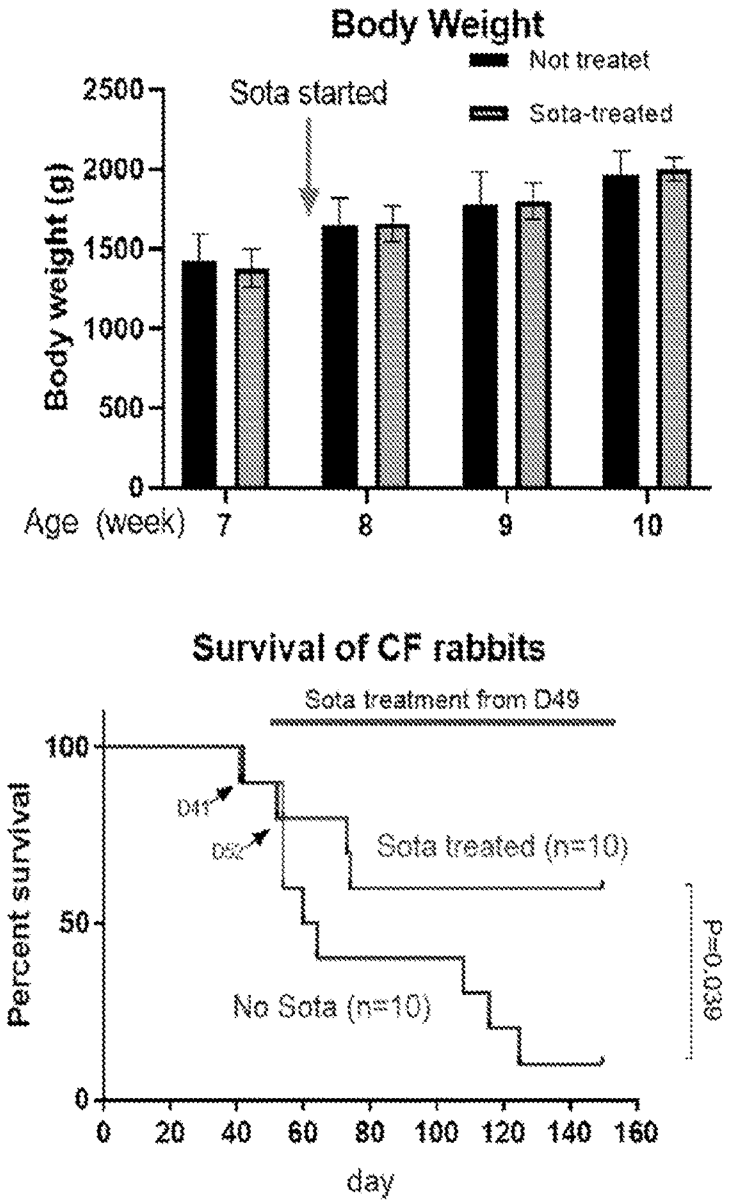
FIG. 12. Body weight (left) and survival curve (right) of Sota-treated CF rabbits.

Sota-treated CF rabbits gained weight at a similar rate to that of animals did not receive the drug (FIG. 12, left panel), suggesting that Sota treatment did not severely affect CF rabbits' nutritional intake.

This is further supported by the elongated lifespan of Sota-treated CF rabbits. CF rabbits without Sota (control group, n=10) had a median lifespan of ~60 days, similar to our earlier findings (with liquid diet supplements). With Sota treatment (starting on Day 49 of age), the CF rabbits (n=10) had a median lifespan >150 days (FIG. 12, right panel), and a significantly greater number of Sota treated CF rabbits (n=6) lived beyond 150 days than those in the control group (n=1). These findings indicate that contrary to the beliefs by many, the SGLT inhibitor drugs are indicative of bringing benefits with minimal risks to CF patients.

Figure 13:
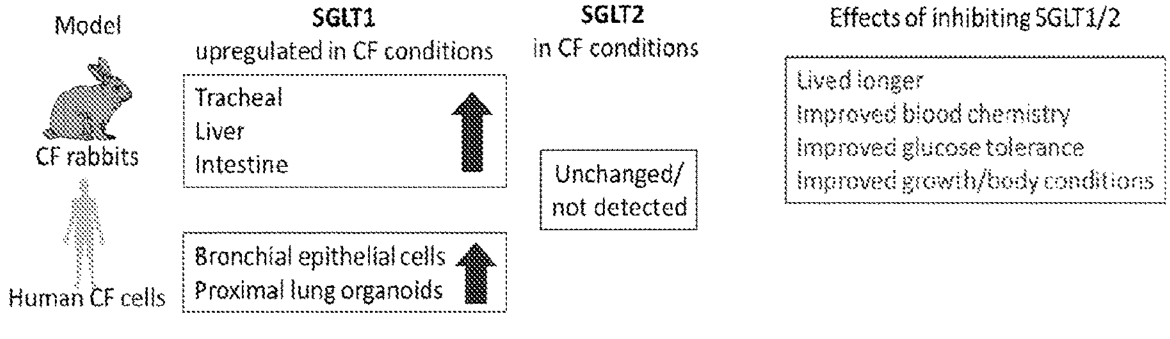
FIG. 13. A summary schematic showing that SGLT1 is upregulated in human CF airway lineage cells, and in many CF relevant tissues in CF rabbits; and that SGLT inhibitor Sota brought many beneficial effects on CF rabbits.

FIG. 13 provides a summary schematic showsing that SGLT1 is upregulated in human CF airway lineage cells, and in many CF relevant tissues in CF rabbits; and that SGLT inhibitor Sota brought many beneficial effects on CF rabbits.

Together, these data show that SGLT1 is upregulated in CF relevant tissues in CF rabbits.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

What is claimed is:

1. A method for treating cystic fibrosis (CF), and/or symptoms related to any form and/or mutation of CF in a human subject, comprising administering to the human subject a composition comprising a pharmaceutical agent capable of inhibiting SGLT1 activity, wherein the pharmaceutical agent is sotagliflozin (LX4211), wherein administration results in an increase in serum albumin level or an increase in total serum protein level of the subject, wherein the one or more symptoms related to CF include one or more selected from hypokalemia, hyperglycemia, dyslipidemia, hypoalbuminemia, and hypoproteinemia.

* * * * *